United States Patent [19]

Rathke et al.

[11] Patent Number: 5,198,589

[45] Date of Patent: Mar. 30, 1993

[54] COBALT CARBONYL CATALYZED OLEFIN HYDROFORMYLATION IN SUPERCRITICAL CARBON DIOXIDE

[75] Inventors: Jerome W. Rathke, Lockport; Robert J. Klingler, Westmount, both of Ill.

[73] Assignee: The United States of America as represented by the United States Department of Energy, Washington, D.C.

[21] Appl. No.: 874,897

[22] Filed: Apr. 28, 1992

[51] Int. Cl.$^5$ .................. C07C 45/50; C07C 29/16
[52] U.S. Cl. ........................... 568/454; 568/451; 568/909
[58] Field of Search ............... 568/451, 454, 456, 840, 568/850, 882, 909

[56] References Cited

U.S. PATENT DOCUMENTS

| | | | |
|---|---|---|---|
| 4,201,728 | 5/1980 | Hughes | 568/454 |
| 4,275,243 | 6/1981 | Saito et al. | 568/454 |
| 4,349,415 | 9/1982 | DeFilippi et al. | 203/14 |
| 4,437,938 | 3/1984 | Bhise et al. | 203/14 |
| 4,492,808 | 1/1985 | Hagen et al. | 568/916 |
| 4,508,928 | 4/1985 | Victor | 568/916 |
| 4,528,404 | 7/1985 | Oswald et al. | 568/454 |
| 5,045,793 | 9/1991 | Rathke | 324/318 |

FOREIGN PATENT DOCUMENTS 2415902 10/1974 Fed. Rep. of Germany.
3415968 10/1985 Fed. Rep. of Germany ...... 568/454

OTHER PUBLICATIONS

R. Fowler et al., "Hydroformylate propylene at low pressure", Hydrocarbon Proc. 55 (9) 247 (1976).
J. W. Rathke et al., "Propylene Hydroformylation in Supercritical Carbon Dioxide", Organometallics 1991, 10, 1350–1355.

*Primary Examiner*—Werren B. Lone
*Attorney, Agent, or Firm*—James W. Weinberger; John M. Albrecht; William R. Moser

[57] ABSTRACT

A method of olefin hydroformylation is provided wherein an olefin reacts with a carbonyl catalyst and with reaction gases such as hydrogen and carbon monoxide in the presence of a supercritical reaction solvent, such as carbon dioxide. The invention provides higher yields of n-isomer product without the gas-liquid mixing rate limitation seen in conventional Oxo processes using liquid media.

13 Claims, 3 Drawing Sheets

COBALT CARBONYL CATALYZED OLEFIN HYDROFORMYLATION IN SUPERCRITICAL CARBON DIOXIDE

CONTRACTUAL ORIGIN OF THE INVENTION

The United States Government has rights in this invention pursuant to Contract No. W-31-109-ENG-38 between the U.S. Government and Argonne National Laboratories.

BACKGROUND OF THE INVENTION

1. Field of the Invention

This invention relates to a method of olefin hydroformylation and more particularly to a method of olefin hydroformylation in supercritical carbon dioxide resulting in higher yields of the n-isomer.

2. Background of the Invention

Large scale conversion of olefins to aldehydes and/or alcohols is a well-known commercial objective. Conversion of ethylene, propylene, butenes and other alkenes ranging from $C_2$–$C_{13}$ and $C_{12}$–$C_{18}$ to aldehydes and alcohols, for example, is necessary to produce more complex molecules for use as plasticizers, detergents and in a myriad of applications. Such conversions of the alkene can be made using the Oxo process wherein olefins react with carbon monoxide and hydrogen in the presence of a catalyst.

There are problems with the conventional Oxo process, however, such as gas-liquid mixing inefficiencies wherein reactive gases do not adequately mix with each other. Gas-liquid mixing problems lower the yield of the desired n-isomer and limit the upper reaction temperature of the process. For example, typical Oxo processes yield isomer selectivity ratios of approximately 3.0:1 to 4:1, or a 75% to 80% n-isomer yield. R. Fowler, H. Connor and R. A. Baehl. *Hydrocarbon Proc.* 55(9), 247 (1976). A need exists in the art to increase n-isomer yields significantly as straight chain products are the desired feed stocks for more complex molecule building.

Another significant shortcoming of the Oxo process is the low concentrations of carbon monoxide and hydrogen in the reaction solvent, leading to low catalysts efficiencies and lower overall product yields.

Conventional Oxo processes suffer from yet another shortcoming wherein the separation of catalysts from products involve energy intensive distillations.

A need exists in the art to provide a hydroformylation process wherein gas-liquid mixing problems are minimized, concentrations of synthesis gases in the reaction solvent are maximized, higher ratios of n-isomer to iso-isomers are achieved, and more efficient separation procedures can be utilized for product and catalyst recovery.

SUMMARY OF THE INVENTION

It is an object of the present invention to provide a method for overcoming many of the disadvantages of the approaches or methods of the prior art.

It is another object of the present invention to provide a method for producing aldehydes and/or alcohols from olefins via the Oxo process. A feature of the present invention is using a supercritical solvent, such as carbon dioxide, as a reaction medium. An advantage of the present invention is that the use of a supercritical solvent eliminates the gas-liquid mixing problems of conventional Oxo processes by creating a homogeneous vapor phase reaction fluid.

Still another object of the present invention is to provide more efficient conversions of olefins to desired aldehydes and alcohols via the Oxo process. A feature of the present invention is higher concentrations of reactive gases. An advantage of the present invention is higher yields and lower costs in producing n-isomer aldehydes and alcohols.

Yet another object of the present invention is to provide a more economical Oxo process. A feature of the present invention is to provide a homogeneous vapor phase reaction environment containing supercritical carbon dioxide. An advantage of the present invention is a more complete and efficient separation of the reaction catalyst from the desired product, due to sharp changes in solubilities of dissolved species with the density of the supercritical $CO_2$.

In brief, the objects and advantages of the present invention are achieved by mixing predetermined pressures of hydrogen and carbon monoxide and predetermined concentrations of an olefin and a carbonyl catalyst together to create a mixture and supplying a supercritical reaction medium to the mixture to create and maintain a homogeneous vapor phase reaction fluid at a predetermined pressure. The objects and advantages of the invention are further met by providing a method of propylene hydroformylation involving mixing predetermined pressures of hydrogen and carbon monoxide and predetermined concentrations of propylene and a cobalt carbonyl catalyst together to create a mixture and supplying supercritical carbon dioxide to the mixture to create and maintain a homogeneous vapor phase reaction fluid at a predetermined pressure.

BRIEF DESCRIPTION OF THE DRAWINGS

The present invention together with the above and other objects and advantages may best be understood from the following detailed description of the embodiment of the invention illustrated in the drawings, wherein.

DETAILED DESCRIPTION OF THE INVENTION

Figure 1:
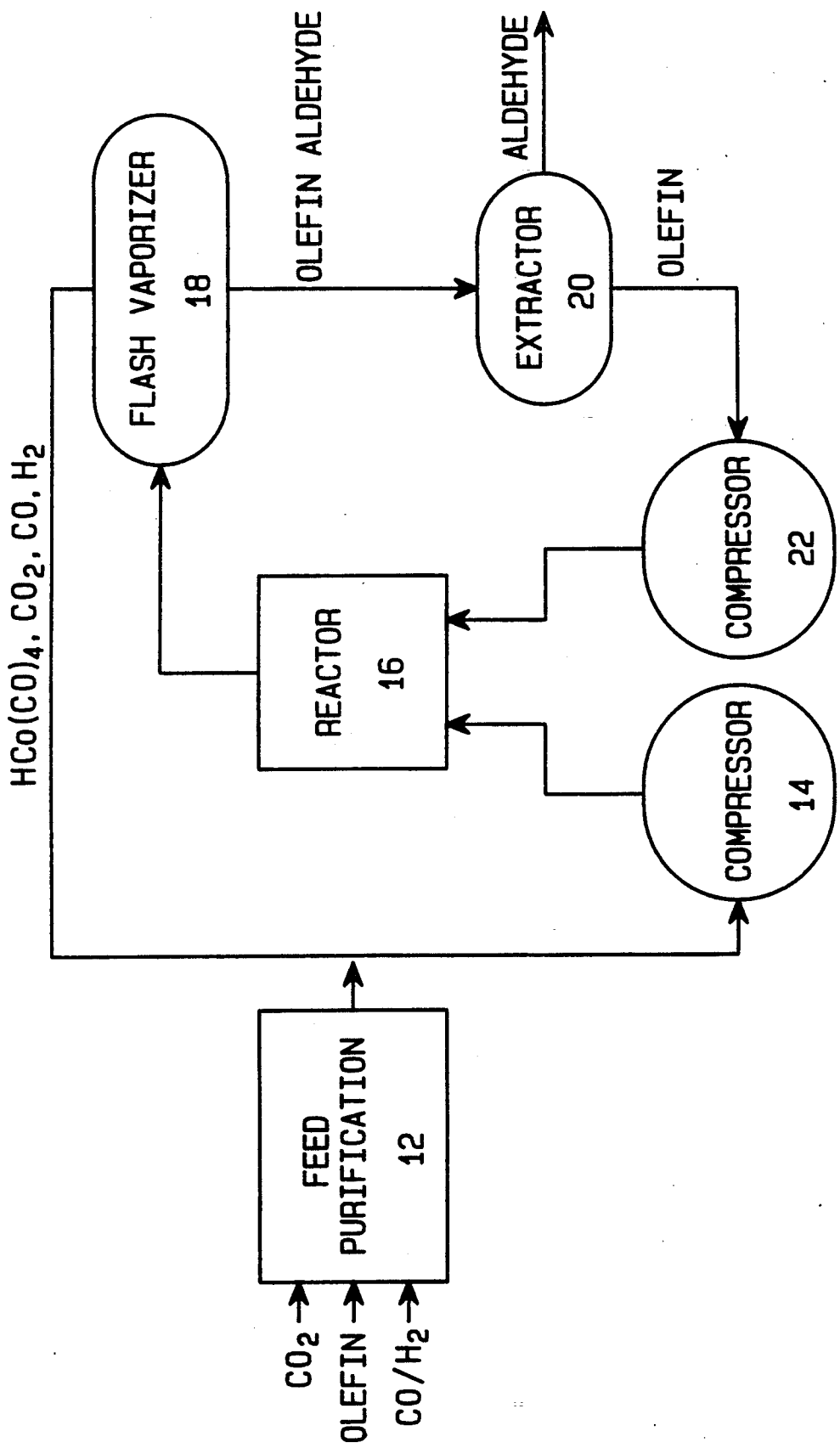
FIG. 1 is a diagram of an exemplary process illustrating the present invention.

Supercritical fluids (i.e., compounds and elements maintained above their critical temperature) have gas-like viscosities that ar frequently one order of magnitude lower than those of typical liquids. For example, at its critical point, carbon dioxide has a viscosity of only 0.025 centipoises (cp) while benzene, at 25° C., has a viscosity of 0.61 cp. This phenomenon is seen even when supercritical fluids are compressed to achieve liquid-like densities.

It has been found quite unexpectedly that the use of a supercritical fluid, such as carbon dioxide, as the reaction medium in Oxo processes improves both the desired product yield and product/catalyst separation efficiencies.

The inventors have found, for example, that the use of supercritical carbon dioxide as a reaction medium in olefin hydroformylation results in a significant increase in the selectivity ratio of the n-isomer to 7.3:1, compared to approximately 4:1 seen in conventional processes, mentioned supra. Table 1 below compared known selectivity ratios, obtained with propylene hydroformylation using conventional solvents, with selectivity ratios experimentally derived, using supercritical $CO_2$. Specifically, it was found that at 80° C., hydroformylation of propylene proceeds cleanly in carbon dioxide providing improved yields of linear to branched butyraldehyde products of 7.3 to 1 (or 88 percent) without use of stirring.

TABLE 1

Selectivity in the Hydroformylation of Propylene

| Solvent | n/i-butyraldehydes |
| --- | --- |
| 2,2,4-Trimethylpentane[a] | 4.6 |
| Benzene[a] | 4.5 |
| Toluene[a] | 4.4 |
| Ethyl ether[a] | 4.4 |
| Ethyl alcohol, 95%[a] | 3.8 |
| Acetone[a] | 3.6 |
| Commercial plants[b] | 3.0–4.1 |
| $CO_2$(0.5 g/mL)[c] | 7.3 |

[a]T = 108° C., P(CO) = 140 atm, p($H_2$) = 100 atm. Data derived from P. Pino, F. Piacenti, M. Bianchi and R. Lazzaroni., Chim. Ind. (Milan) 50, 106 (1968).
[b]T = 140–180° C., P(CO) = 100–150 atm, P($H_2$) = 100–150 atm. Data derived from R. Fowler, H. Connor and R. A. Baehl., Hydrocarbon Proc. 55(9), 247 (1976).
[c]T = 80° C., P(CO) = 56.1 atm, P($H_2$) = 56.1 atm. Experimentally derived.

A number of patents, among them U.S. Pat. Nos. 4,437,938; 4,349,415; and 4,492,808, teach using carbon dioxide in processes for separating organic solutes from reaction liquors. There are also reports, among the German patents 3,415,968 and 2,415,902, disclosing the use of carbon dioxide as an additive to improve the yield of aldehydes or alcohols when using a rhodium based catalyst or a phosphine modified cobalt catalyst. However, nothing in the literature suggests using supercritical $CO_2$ as a reaction medium in Oxo processes.

Kinetic and equilibrium constant measurements presented infra were conducted in the in situ mode using a General Electric GN 300/89NMR spectrometer equipped with a homebuilt pressure probe, the later of which is disclosed in U.S. Pat. No. 5,045,793, assigned to the applicants and incorporated herein by reference. The probe was used to record spectra of HCo(CO). in supercritical $CO_2$ at a total pressure of 338 atmospheres (atm) at 205° C.

Automated magnet shimming and spectral observations were commenced 15 minutes (the interval required for a complete thermal equilibration) after heating the closed system to the desired reaction temperature.

Method of Aldehyde and Alcohol Formulation

Referring to FIG. 1, there is shown a method for producing higher n-isomer yields in the Oxo process by using a supercritical fluid, such as supercritical $CO_2$, in a process designated by the reference numeral 10. The process 10 involves first a purification step 12 wherein an olefin, CO, $H_2$ and the reaction solvent are treated, prior to pressurization.

After pressurization using a compressor 14, the reactive gases CO, $H_2$, an olefin and a supercritical solvent are admitted into a reactor 16, such as any standard pressure vessel, containing a carbonyl catalyst. Alternatively, the catalyst can be added simultaneously with the reactive gases into the reactor 16. Also, the supercritical solvent can be added to the reactor 16 after the reactive gases and carbonyl catalyst are already loaded into the reactor 16. Whatever the loading sequence used, however, it is suggested that the temperature of the reactor 16 is such that the $CO_2$, or another reaction solvent, is maintained above its critical temperature to prevent liquid formation.

The mixture reacts for a predetermined period of time and is then distilled in a flash vaporizer 18. Formulated aldehyde and alcohol and unreacted olefin are then separated via an extractor 20, with the olefin being repressurized by a feedback compressor 22 and readmitted into the reactor 16 with additional and unspent reactive gases.

Catalyst Types and Function: A myriad of carbonyl catalysts can be used in the invention. Generally, the stability of carbonyl catalysts depends upon carbon monoxide pressures and also the temperature inside the reactor.

As such, the method of combining all reactive gases and the supercritical solvent prior to addition of a carbonyl catalyst, as depicted in FIG. 1, is just one method of mixing.

Generally, between 0.001 and 0.020 moles/liter (M) of catalyst is used, preferably 0.005 M.

Cobalt. The hydroformylation reaction is catalyzed homogeneously by carbonyls of Group VIII metals, but there are significant differences in their relative activities. Cobalt has good hydroformylation activity, and dicobalt octacarbonyl, $Co_2(CO)_8$, which either is introduced directly or formed in situ, is a good Oxo catalyst precursor. In solution and under Oxo reaction conditions, the octacarbonyl is in equilibrium with hydrocobalt tetracarbonyl, $HCo(CO)_4$, and with hydrocobalt tricarbonyl, $HCo(CO)_3$, as shown in equations 1 and 2:

$$Co_2(CO)_8 + H_2 \rightleftharpoons 2HCo(CO)_4 \qquad \text{Eq. 1}$$

$$HCo(CO)_4 \rightleftharpoons HCo(CO)_3 + CO \qquad \text{Eq. 2}$$

Dicobalt octacarbonyl is formed readily by the reaction of metallic cobalt, cobalt oxide, cobalt carbonate, or a cobalt soap with hydrogen and carbon monoxide. The octacarbonyl is an orange crystalline solid in which two CO molecules serve as bridging ligands for the Co atoms.

Rhodium. Rhodium carbonyl catalysts are also very reactive. Simple rhodium carbonyl hydroformylation catalysts tend to favor branched chain products, but linear products at lower pressures can be obtained with rhodium carbonyl-phosphine complex catalysts.

Complexes, such as hydrorhodium carbonyl tris(triphenylphosine), are highly reactive homogenous catalysts yielding high amounts of the n-isomers at relatively lower temperatures and pressures.

Other metals complexes having good catalytic potential include ruthenium tricarbonyl bis(triphenylphosphine) and the platinum complex carbonylhydrobis(triphenlyphosphine platinum trichlorostannate); i.e., PtH $(SnCl_3((CO)[P(C_6H_5)_3]_2$.

Pressures and Temperatures: While the supercritical media used in experiments by the inventors was supercritical $CO_2$, other reaction media, such as supercritical ethane, propane and xenon, are suitable solvents. Carbon dioxide is particularly attractive a it is an inexpensive solvent, compatible with the reactants, does not interfere in the reaction, and may improve equilibrium values.

Experiments with supercritical $CO_2$ were initiated by admitting the required pressures of reactive gases, measured to within ±0.07 atm by using a strain-gauge pressure transducer (Omega Model PX302-5KGV), into the reactor 16 containing a weighed amount of $Co_2(CO)_8$. Pressures and concentrations of reactive gases varies with the ultimate product desired. For aldehyde and alcohol production, pressures of CO and hydrogen range from 25 to 300 atm, preferably 150 atm; and for $CO_2$, pressures range from 50 to 100 atm, preferably 75 atm. Olefin feed concentrations can range from 0.5 to 5M, preferably 2.5 M. Maximum pressures within the reactor 16 can range from 100 to 700 atm, preferably 375 atm. The use of phosphine-ligand cobalt carbonyl catalysts or rhodium-containing catalysts can reduce pressure requirements considerably in this process Temperatures for these reactive gases can range from approximately 80° C. to 180° C., preferably 150° C.

After introduction of the reactive gases, the reactor 16 was then preheated to 34° C., which is above the critical temperature of $CO_2$ (31° C.), and $CO_2$ was added by means of a high-pressure syringe pump (not shown) until the measured pressure increase was 82 atm, thereby achieving fluid density in the reactor of approximately 0.5 grams per milliliter (g/mL). A range of fluid densities can be employed, ranging from 0.5 to 1 g/mL. A temperature slightly above the critical temperature of $CO_2$ (31.2° C.) was used for the addition to ensure complete vaporization, thereby avoiding a potentially hazardous pressure surge that could be generated by the syringe pump were the reactor 16 to inadvertently fill with liquid which is less compressible than vapor. Generally, the temperature of $CO_2$ should range from between 80 and 180° C., preferably 150° C. during its addition into the reactor 16. In commercial scale processes, the compressor 14 or similar device would supplant the pressure syringe pump as the vehicle for admitting supercritical solvents into the reactor 16.

Complete dissolution of $Co_2(CO)_8$ in $CO_2$ at the above indicated density required 2.5 hours at 34° C. as determined by monitoring its $^{59}Co$ signal at $\delta = -220$ ppm (saturated aqueous $K_3Co(CN)_6 = 0.0$ ppm). Concentrations greater than 0.1 M were easily obtained.

EXAMPLE 1

Propylene Hydroformylation

Figure 2:
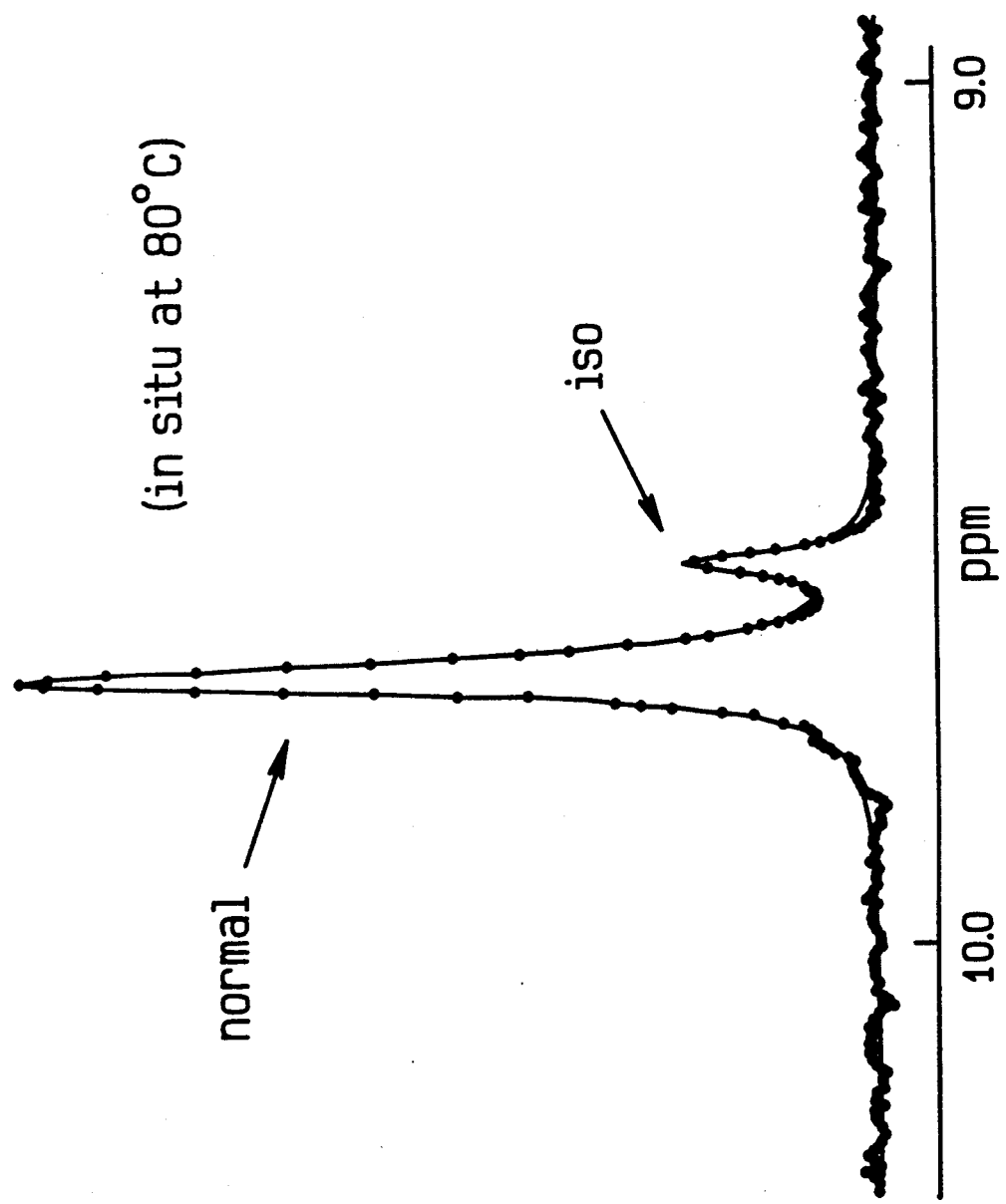
FIG. 2 is a H NMR spectrograph depicting relative yields of n-isomer to branched isomers as produced by the invention.

At 80° C. in supercritical carbon dioxide (d=0.5 grams per milliliter) using the conditions, $[Co_2(CO)_8]_i = 0.017$ M, $P_{H2} = P_{CO} = 42$ atm, $[C_3H_6] = 0.14$ M, propylene hydroformylation proceeds cleanly, yielding only the expected n- and iso-butyraldehyde products which were measured by integration of their characteristic proton signals near $\delta = 9.8$ and 9.6 ppm, respectively, as depicted in FIG. 2.

For the propylene hydroformylation conditions given in Table 2 below, the relative yield of n-butyraldehyde, determined by integration of the previously mentioned proton signals for the linear and branched isomers, is 7.3 to 1. This compares favorably with a 4:1 n-isomer yield that is obtained when a benzene media is utilized at different temperatures and pressures.

TABLE 2

| Observable Parameters During Hydroformylation At 80° C. | | | | |
|---|---|---|---|---|
| conditions | $[Co_2-(CO)_8]ss'$ mM | $[HCo-(CO)_4]ss'$ mM | [acyl]ss' mM | d[aldehyde]/dt, Ms-1 |
| a | 4.6 | 1.3 | 2.7 | $1.2 \times 10^{-5}$ |

TABLE 2-continued

| Observable Parameters During Hydroformylation At 80° C. | | | | |
|---|---|---|---|---|
| conditions | $[Co_2-(CO)_8]ss'$ mM | $[HCo-(CO)_4]ss'$ mM | [acyl]ss' mM | d[aldehyde]/dt, Ms-1 |
| b | 8.4 | 3.5 | 0.8 | $0.77 \times 10^{-5}$ |

<sup>a</sup>For reaction of 1-ocetene, 0.83 M, in methylcyclohexane, $[Co_2 - (CO)_8]_i = 6.6$ mM, $P_{H2} = P_{CO} = 47.5$ atm.
<sup>b</sup>For reaction of propylene, 0.53 M, in $CO_2$ (d = 0.5 g/mL), $[CO_2(CO)_8]_i = 10.5$ mM, $P_{H2} = P_{CO} = 56.1$ atm.
ss = steady state concentrations.

Comparison of Liquid and Supercritical Media

Unlike conventional Oxo processes, which employ liquid media as solvents, when supercritical carbon dioxide is substituted for such solvents, only one phase is present in the reaction chamber. As this phase contains higher reactive gas concentrations compared with conventional liquid media at the same hydrogen and carbon monoxide partial pressures, gas depletion effects are minimized. The diffusivities of small molecules in carbon monoxide at its critical point are 1 to 2 orders of magnitude higher than typical values for solutes in organic liquids which average $10^{-5}$ square centimeters per second (cm$^2$/s). It was observed also that when $H_2$ pressurized at 100 atm is combined with a liquid ($C_6D_6$, 7.0 mL), the hydrogen dissolution rate is far too slow for all but the most sluggish of hydrogen consuming reactions. Even without stirring, an equilibrium distribution of gases in the vapor or a supercritical fluid phase prevails shortly after pressurization.

Also, high concentrations of hydrogen were observed in supercritical environs. At 25° C. and a partial pressure of 300 atm in supercritical carbon dioxide, hydrogen concentration is 12 molar (M), while in water and in n-heptan the hydrogen concentrations under these conditions are only 0.23 and 1.8 M, respectively. In the vapor phase, a hydrogen concentration of 4.1 M is more than one order of magnitude higher than the value measured in the liquid $C_6D_6$ at saturation (0.31 M). The increased saturation and concentration values observed in supercritical fluids facilitates fast reactions that involve gases and, in rate measurements, obviate the need for special stirring mechanisms which otherwise would be required.

Supercritical fluids, even when compressed to achieve liquid-like densities, have gas-like viscosities that are frequently one order of magnitude lower than those of typical liquids.

Equilibrium and Dynamic Processes in Supercritical $CO_2$

Figure 3:
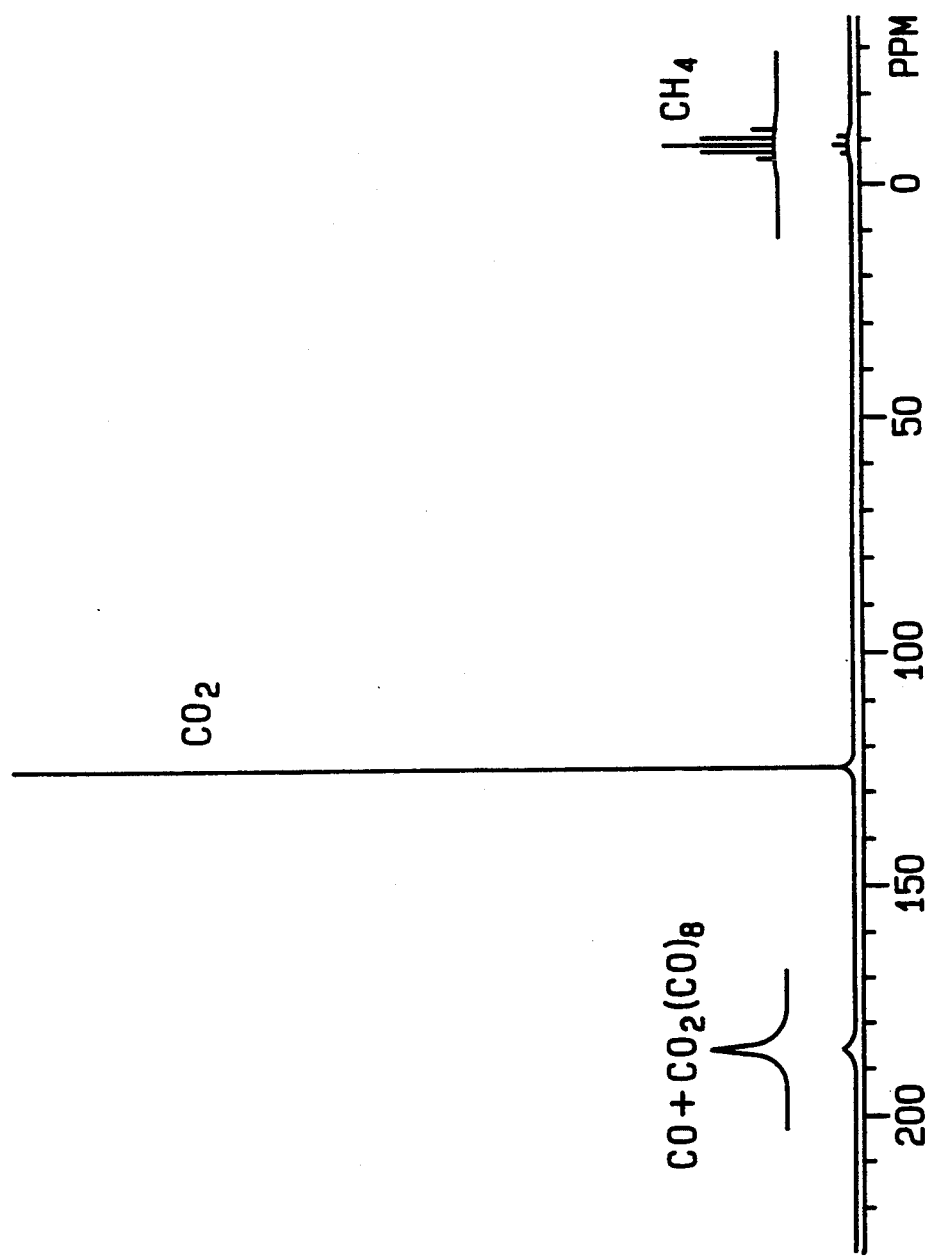
FIG. 3 is a $^{13}C$ NMR spectrograph depicting free and combined CO resonances in supercritical $CO_2$.

Carbon dioxide does not interact strongly with cobalt carbonyls. Indeed, it was observed that CO: concentrations do not change significantly after completion of gas addition. Furthermore, at the high temperatures of carbon monoxide used in this Oxo process, $CO_2$ participation in the equilibria in exchange processes that occur with the carbonyls and $H_2$ and CO are negligible. Under conditions where carbon monoxide exchange is rapid, the $CO_2$ resonance, typically having a value of 126 ppm (C=11 M) remains sharp indicating that $CO_2$ exchange is comparatively slower or at least less extensive than exchange with CO. In addition, the normally separate $^{13}$Carbon resonance measured at 34° C. for free CO ($\delta = 185$ ppm, C = 1.14 M, $P_{CO} = 35$ atm) and coordinated CO in $Co_2(CO)_8$ ($\delta = 201$ ppm, $[Co_2(CO)_8] = 0.03$ M), coalesce at 145° C. to form a broad singlet near 186 ppm as shown in FIG. 3.

In the presence of $H_2$, equilibration of $Co_2(CO)_8$ to form $HCo(CO)_4$ (as depicted in equation 3, below) appears normal in supercritical $CO_2$.

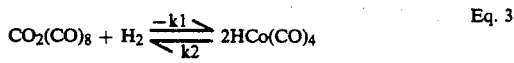

Eq. 3

The rate of propylene hydroformulation and the in situ measurements of the steady-state concentrations of catalytic intermediates [$RC(O)Co(CO)_4$), $HCo(CO)_4$, and $Co_2(CO)_8$] were found to be comparable to values reported in the literature for other linear-terminal olefins in nonpolar liquid media. For the hydrogenation of $Co_2(CO)_8$ to yield $HCo(CO)_4$ at 80° C. in supercritical carbon dioxide, the equilibrium constant, $K_P = 8.8 \times 10^{-4}$ M atm$^{-1}$, and the forward and reverse rate constants, $1.6 \times 10^{-6}$ atm, $^{-1}s^{-1}$ and $1.8 \times 10^3 M^{-1}s^{-1}$, respectively were measured The enthalpy and entropy changes, $4.7 \pm 0.2$ kcal/mol and $4.4 \pm 0.5$ cam/mol K, respectively, were determined over the temperature range of 60–180 C. The kinetic and thermodynamic values measured in supercritical carbon dioxide are in good agreement with reported value in conventional hydrocarbon solvent systems.

Obviously, many modifications and variations of the present invention ar possible in light of the above teachings. Thus, it is to be understood that, within the scope of the appended claims, the invention may be practiced otherwise than as specifically described above.

What is claimed and desired to be secured by Letters Patent of the United States is:

1. A method of olefin hydroformylation to produce n-isomer aldehydes and n-isomer alcohols comprising:
   mixing hydrogen and carbon monoxide each at pressures of between approximately 25 to 300 atm, a concentration of an olefin of the type having the generalized formula $C_nH_{2n}$ at aq concentration ranging from approximately 0.5 to 5 moles per liter and a concentration of between approximately 0.001 to 0.02 moles/liter of a carbonyl catalyst containing a transition metal together to create a mixture;
   supplying a supercritical reaction media to the mixture to create and maintain a homogeneous vapor phase reaction fluid at a pressure ranging from approximately 100 to 700 atm; and
   extracting the n-isomer aldehydes and n-isomer alcohols from the reaction fluid.

2. The method as recited in claim 1 wherein the olefin is selected from the group consisting of ethylene, propylene, butene, pentene, alkenes having from six to eighteen carbons, and combinations thereof.

3. The method as recited in claim 1 wherein the carbonyl catalyst contains a Group VIII metal.

4. The method as recited in claim 3 wherein the Group VIII metal is selected from the group consisting of cobalt, rhodium, ruthenium, platinum, and combinations thereof.

5. The method as recited in claim 1 wherein the carbonyl catalyst contains a phosphine ligand.

6. The method as recited in claim 1 wherein the supercritical reaction medium is selected from the group consisting of carbon dioxide, ethane, propane, xenon and combinations thereof.

7. The method as recited in claim 1 wherein mixing hydrogen, carbon monoxide, an olefin and the carbonyl catalyst together and supplying supercritical reaction medium to the mixture comprises the additional steps of:
   containing the carbonyl catalyst in a reactor;
   admitting the carbon monoxide and hydrogen into the reactor;
   admitting the olefin into the reactor;
   maintaining the temperature of the reactor above the critical temperature of the supercritical reaction medium; and
   supplying the supercritical reaction medium to the reactor to bring the inside of the reactor to a predetermined pressure.

8. The method as recited in claim 6 wherein the temperature of the reaction mixture ranges from approximately 80° C. to 180° C.

9. A method as recited in claim 1 wherein the carbonyl catalyst containing a transition metal is selected from the group consisting of dicobalt octacarbonyl, hydrorhodium carbonyl tris(triphenylphosphine), ruthenium tricarbonylbis(triphenylphosine), carbonylhydrobis(triphenylphosphine platinum trichlorostannate), and combinations thereof.

10. A method of propylene hydroformylation to form n-butyraldehyde and n-butanol comprising:
    mixing pressurized hydrogen, pressurized carbon monoxide, each at pressures of between approximately 25 and 300 atmospheres, propylene in a concentration of between approximately 0.25 to 5 moles per liter, and a cobalt carbonyl catalyst in a concentration of between approximately 0.001 and 0.02 moles/liter together to create a mixture under pressure;
    supplying supercritical carbon dioxide to the mixture to create and maintain a homogeneous vapor phase reaction fluid at a pressure between 100 and 700 atm; and
    extracting newly formed n-butyraldehyde and n-butanol from the reaction fluid.

11. The method as recited in claim 10 wherein the temperature of the reaction mixture ranges from approximately 80° C. to 180° C.

12. The method as recited in claim 10 wherein the concentration of the homogeneous vapor phase reaction fluid is between 0.5 and 1 g/mL.

13. A method as recited in claim 10 wherein the cobalt carbonyl catalyst is dicobalt octacarbonyl.

* * * * *